(12) United States Patent
Chisholm (10) Patent No.: US 7,972,290 B1
(45) Date of Patent: Jul. 5, 2011

(54) DYNAMIC FOOT-ARCH SUPPORT SYSTEM AND ASSOCIATED METHODS

(76) Inventor: Donna Chisholm, Dalzell, SC (US)

( * ) Notice: Subject to any disclaimer, the term of this patent is extended or adjusted under 35 U.S.C. 154(b) by 188 days.

(21) Appl. No.: 12/029,503

(22) Filed: Feb. 12, 2008

(51) Int. Cl.
*A61F 13/00* (2006.01)
(52) U.S. Cl. ............... 602/66; 602/60; 602/62
(58) Field of Classification Search .............. 602/65, 602/66, 20–22; 66/178, 185; 2/239; 36/8.3, 36/102
See application file for complete search history.

(56) References Cited

U.S. PATENT DOCUMENTS

| | | | |
|---|---|---|---|
| 1,441,907 A * | 1/1923 | Bernstein | .................. 602/65 |
| 2,708,930 A | 5/1955 | Lowman | |
| 4,084,586 A | 4/1978 | Hettick | |
| 4,085,745 A | 4/1978 | Alenares | |
| 4,597,395 A | 7/1986 | Barlow | |
| 5,460,601 A | 10/1995 | Shannahan | |
| 5,473,781 A | 12/1995 | Greenberg | |
| 5,928,173 A * | 7/1999 | Unruh | .......................... 602/30 |
| 6,886,276 B2 | 5/2005 | Hlavac | |
| 7,346,936 B2 * | 3/2008 | Vargas et al. | ................... 2/239 |
| 2008/0034613 A1 * | 2/2008 | Wilkenfeld et al. | ............ 36/8.3 |

* cited by examiner

*Primary Examiner* — Kim M Lewis
(74) *Attorney, Agent, or Firm* — George R. Reardon (57) ABSTRACT

A dynamic foot-arch support device for dynamically supporting the arch and structures of the human foot throughout phases of the biomechanical movement of the foot during weight-bearing activities is provided. A dynamic foot-arch support device for supporting the arch and structures of a foot is provided that includes a support band having an upper end and a lower end, the support band forming a loop at the upper end through which to place a foot and position the loop around or just below an ankle portion of the foot, the lower end configured to wrap from an inside area of the ankle portion of the foot and rotate to an underside of the foot for secure attachment below the underside of the foot, the support band thereby configured to provide a tension to support to an arch area of the foot.

2 Claims, 8 Drawing Sheets

DYNAMIC FOOT-ARCH SUPPORT SYSTEM AND ASSOCIATED METHODS

FIELD OF THE INVENTION

The technology described herein relates generally to support devices for protecting anatomical parts. More specifically, the technology described herein relates to a dynamic foot-arch support device, and associated methods, for dynamically supporting the arch and structures of the human foot throughout phases of the biomechanical movement of the foot during weight-bearing activities.

BACKGROUND OF THE INVENTION

The human feet endure a multiplicity of strong forces in order to support and balance the weight of the entire body during ordinary daily activities. In fact, the feet are the primary weight-bearing elements of the upright body. By way of example, supporting the arch and structures in the feet aids a person who is standing, walking, running, etc. Additionally, such support can decrease undesired stresses upon the arch and structures of the feet.

These and other problems exist. Previous attempts to solve these and other problems include the following. U.S. Pat. No. 4,085,745, issued to Alenares on Apr. 25, 1978, discloses an elastic support for the veins of the foot. U.S. Pat. No. 6,886,276, issued to Hlavac on May 3, 2005, discloses a plantar fascia support apparatus. U.S. Pat. No. 5,473,781, issued to Greenberg on Dec. 12, 1995, discloses a sock having a foot arch support. U.S. Pat. No. 4,084,586, issued to Hettick on Apr. 18, 1978, discloses a tubular support for enclosing a body member. U.S. Pat. No. 5,460,601, issued to Shannahan on Oct. 24, 1995, discloses an elastic footwrap. U.S. Pat. No. 1,512,218, issued to Goldsmith on Oct. 23, 1922, discloses an arch supporter. U.S. Pat. No. 2,708,930, issued to Lowman on Jun. 23, 1952, discloses an arch maintaining device. U.S. Pat. No. 982,664, issued to Fischer on Jan. 24, 1911, discloses a foot glove brace. U.S. Pat. No. 1,365,512, issued to Lewis on Jan. 11, 1921, discloses a device for supporting fallen arch of feet. U.S. Pat. No. 1,220,724, issued to Burns on Mar. 27, 1917, discloses a device for correcting deformities of the feet. U.S. Pat. No. 1,565,259, issued to Collis on Dec. 15, 1925, discloses a combined instep and arch support. U.S. Pat. No. 1,727,586, issued to Condon on Sep. 10, 1929, discloses a stocking protector. U.S. Pat. No. 4,597,395, issued to Barlow on Jul. 1, 1986, discloses an ankle support including a heel lock and a crossover strap.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

BRIEF SUMMARY OF THE INVENTION

In various exemplary embodiments, the technology described herein provides a dynamic foot-arch support device for dynamically supporting the arch and structures of the human foot throughout phases of the biomechanical movement of the foot during weight-bearing activities.

In one exemplary embodiment, the technology described herein provides a dynamic foot-arch support device for supporting the arch and structures of a foot. The dynamic foot-arch support device includes a support band having an upper end and a lower end, the support band forming a loop at the upper end through which to place a foot and position the loop around an area about or just below an ankle portion of the foot, the lower end configured to wrap from an inside of the area about or just below the ankle portion of the foot and rotate to an underside of the foot and across a plantar surface area for secure attachment below the underside of the foot, the support band thereby configured to provide a tension to support to an arch area of the foot. The support band is configured to provide a supportive, counter-reactive force to the arch and structures of the foot during biomechanical movement of the foot during weight-bearing activities. The arch area of the foot is sustained as the foot alternates between weight-bearing and non-weight-bearing activities.

In one embodiment, the support band of the dynamic foot-arch support device is an elongated, flexible elastic strap. A length of the support band is adjustable to accommodate varying foot sizes.

The dynamic foot-arch support device also includes a forefoot cover securely attached to the lower end of the support band and configured for placement over a toe area of the foot, wherein the tension is formed on the support band between the forefoot cover and the loop placed around an area about or just below an ankle portion of the foot providing support to the plantar surface. In one embodiment, the lower end of the support band is securely attached to the forefoot cover at a predetermined angle to maximize support to a plantar portion of the foot.

Alternatively, the lower end of the support band is configured for secure attachment to an inside sole area of a shoe. The tension is formed on the support band between the inside sole area and the loop around an area about or just below an ankle portion of the foot providing support to the plantar surface. Alternatively, the support band is integrally formed with a sock.

In another exemplary embodiment, the technology described herein provides a method for supporting the arch and structures of a foot. The method includes utilizing a support band having an upper end and a lower end, forming a loop at the upper end of the support band through which to place a foot and position the loop around an area about or just below an ankle portion of the foot, configuring the lower end to wrap from an inside of the area about or just below the ankle portion of the foot and rotate to an underside of the foot and across a plantar surface area for secure attachment below the underside of the foot, and configuring the support band to provide a tension to support to an arch area of the foot. The method also includes providing biomechanical arch and foot support with a supportive, counter-reactive force to the arch and structures of the foot during biomechanical movement of the foot during weight-bearing activities. The method also includes providing support to the arch area of the foot as the foot alternates between weight-bearing and non-weight-bearing activities. The support band is an elongated, flexible elastic strap. A length of the support band is adjustable to accommodate varying foot sizes.

The method also includes utilizing a forefoot cover, attaching the forefoot cover securely to the lower end of the support band, and configuring the forefoot cover for placement over a toe area of the foot. The tension is formed on the support band between the forefoot cover and the loop placed around an area about or just below an ankle portion of the foot providing support to the plantar surface. The method also includes attaching the lower end of the support band to the forefoot cover at a predetermined angle to maximize support to a plantar portion of the foot.

Alternatively, the method also includes configuring the lower end of the support band for secure attachment to an inside sole area of a shoe. The tension is formed on the support band between the inside sole area and the loop around an area about or just below an ankle portion of the foot providing support to the plantar surface. Alternatively, the support band is integrally formed with a sock.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides a dynamic foot-arch support device for dynamically supporting the arch and structures of the human foot throughout phases of the biomechanical movement of the foot during weight-bearing activities.

Figure 1:
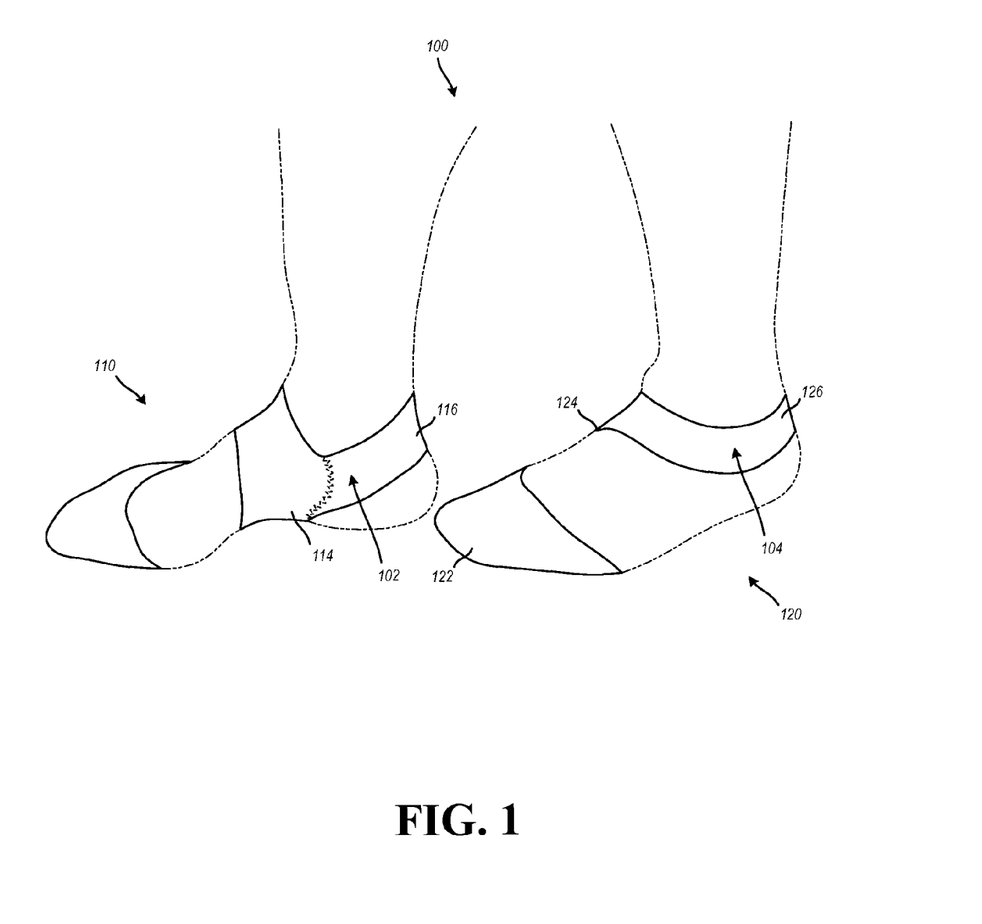
FIG. 1 is a front perspective medial (shown on a right foot) view and lateral (shown on a left foot) view of a dynamic foot-arch support device, according to an embodiment of the technology.
Figure 2:
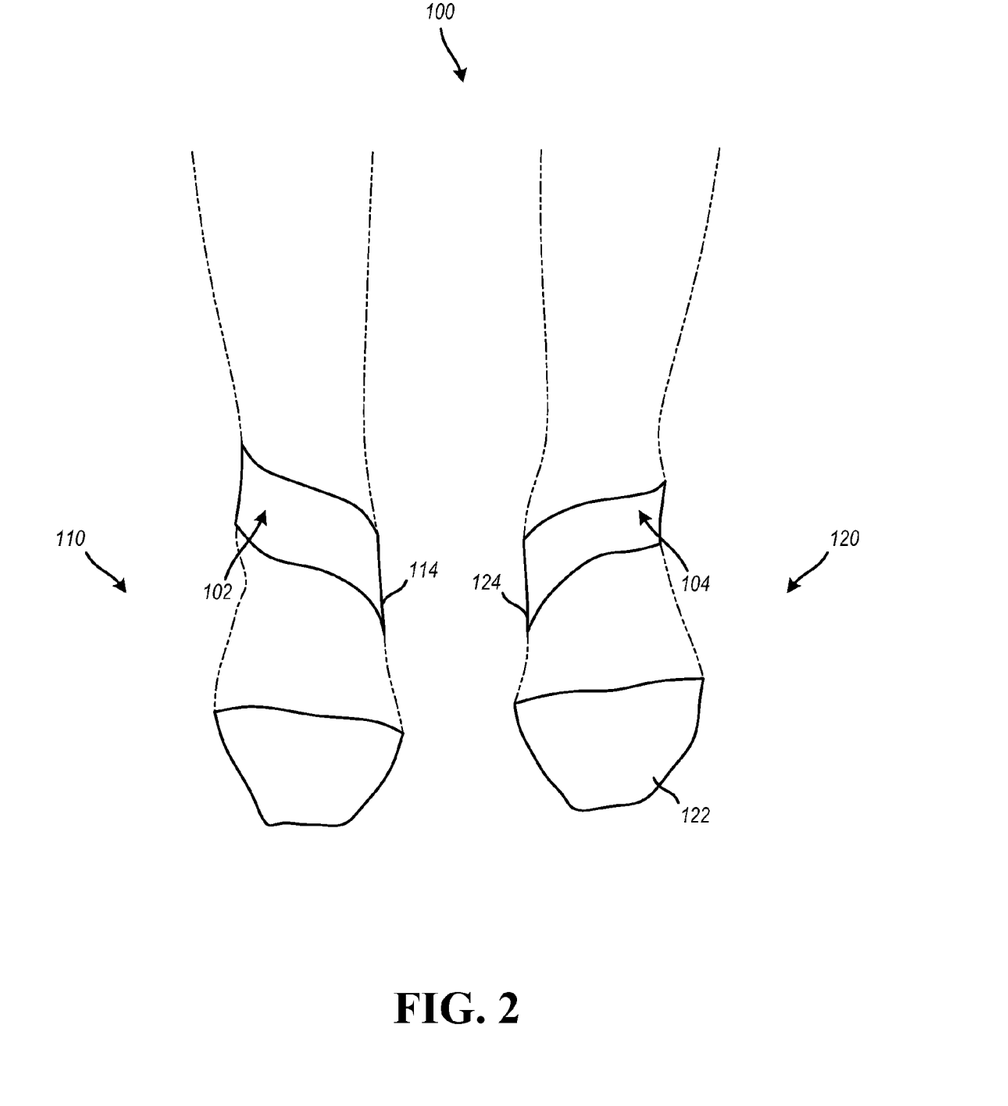
FIG. 2 is a top view of the dynamic foot-arch support device depicted in FIG. 1.

Referring now to FIGS. 1-8, a dynamic foot-arch support device 100 for supporting the arch and structures of a foot is shown. As depicted in FIG. 1, a dynamic foot-arch support device 100 is provided. The dynamic foot-arch support device 100 is suitable for, and is shown on, both a right foot 110 and a left foot 120. The dynamic foot-arch support device 100 is a supportive piece of footwear designed for general use by wearers performing weight-bearing activities such as, for example and not limited to, dynamic standing, walking, jogging, or running. The dynamic foot-arch support device 100 provides intimate support contact to the foot thereby providing support to the arch and other structures of the foot through the biomechanical phases of foot movement.

The dynamic foot-arch support device 100 provides biomechanical arch and foot support with a supportive, counter-reactive force to the arch and structures of the foot during biomechanical movement of the foot during weight-bearing activities. The dynamic foot-arch support device 100 also provides support to the arch area of the foot as the foot alternates between weight-bearing and non-weight-bearing activities.

Figure 8:
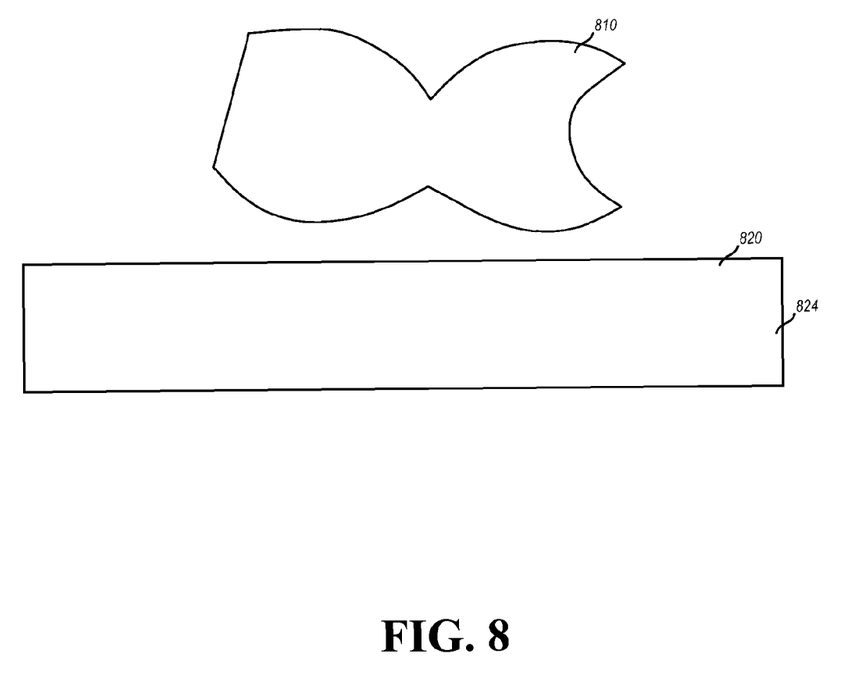
FIG. 8 is a top, planar view of the band and forefoot cover depicted in FIG. 7.

The dynamic foot-arch support device 100 includes a support band 102 (on the right foot), 104 (on the left foot) generally of the original shape 820 as shown in FIG. 8. The biomechanical support to the arch and structures of the foot is provided by the functional design of the support band 102, 104 and by the flexible material with which the support band 102, 104 is fabricated. The support band 102, 104 is generally rectangular in shape and includes two ends, and upper end 822, and a lower end 824, as depicted in FIG. 8. Length of the support band 102, 104 is varied to accommodate varying foot sizes. Width of the support band 102, 104 also is varied to accommodate varying foot sizes. Additionally, the length of the support band can be adjustable on the dynamic foot-arch support device 100 to accommodate varying foot sizes. In one embodiment, the support band 102, 104 is an elongated, flexible elastic material. The flexible elastic material can be, for example, elastic in length and inelastic in width, among other combinations, to provide various support methods to the arch and structures of the foot.

The support band 102, 104 includes a loop formed at the upper end 822 through which to place a foot. The loop is positioned around an area about or just below an ankle portion of the foot. By way of example, the upper end 822 is stitched and attached to a lateral side of the support band 102, 104 to form a top loop for placement around or just below the ankle of the wearer. The opening created by the loop provides for proper placement of the support band 102, 104 about the ankle and the medial arch. By way of example, the loop in the support band 102, 104 shown is placed to rest just below the medial and lateral ankle bones. Alternatively, the support band 102, 104 and loop are integrally formed in a single molded piece that does not require stitching, or the like, to create a loop.

The lower end 824 of the support band 102, 104 is configured to wrap from the medial arch area about or just below the medial, or inside, ankle portion of the foot and be rotated to an underside of the foot and cross diagonally across the plantar surface area for secure attachment below the underside of the foot, providing tension to support to an arch area of the foot. For example, the lower end 824 of the support band 102, 104 terminates under the metatarsal phalange distal heads.

As depicted in FIGS. 1-7, the support band 102, 104 with a loop formed in it has a heel bone portion 116, 126, a medial arch portion 114, 124, and a forefoot portion 118, 128 about both a right foot 110 and a left foot 120. By way of example, the wearer's foot is placed through the loop portion of the support band 102, 104 with the heel bone portion 116, 126 covering the area of the heel bone and the Achilles tendon area. The medial arch portion 114, 124 wraps from the medial ankle portion of the foot to the underside of the foot to traverse diagonally across the plantar surface area. The forefoot portion 118, 128 is utilized for attachment to footwear, a sock, a stocking, a forefoot cover, or the like, providing tension in the support band to support to an arch area of the foot.

In various embodiments, the dynamic foot-arch support device 100 includes a forefoot cover 112, 122. The forefoot cover 112, 122 is an accessory to the support band. The forefoot cover 112, 122 is cut in the general shape of 810 as depicted in FIG. 8. A flexible, comfortable material in the shape of 810 can be folded and stitched to provide a forefoot cover 112, 122. A forefoot cover 112, 122 is securely attached to the forefoot portion 118, 128 of the support band 102, 104 and configured for placement over a toe area of the foot. Tension is formed on the support band between the forefoot cover 112, 122 and the loop placed around an area about or just below an ankle portion of the foot providing support to the plantar surface. By way of example, a wearer of the dynamic foot-arch support device 100 with a forefoot cover 112, 122 places the support band 102, 104 on each foot 110, 120 and then rotates the support band 102, 104 for 180 degrees of rotation and placing the support band 102, 104 on the medial arch before placing the forefoot cover 112, 122 over the toes on each foot.

In one embodiment, the support band is attached to the forefoot cover 112, such that the forefoot portion 118, 128 of the support band is positioned across the plantar surface of the foot and placed distally to rest under the metatarsal phalange distal heads of the plantar surface of the foot. By way of example, the forefoot portion 118, 128 of the support is placed to rest under the $2^{nd}$ through the $4^{th}$ or $5^{th}$ metatarsal phalange distal heads. The forefoot portion 118, 128 of the support band is securely attached to the forefoot cover 112, 122 at a predetermined angle to maximize support to the arch portion of the foot. The predetermined angle of placement can be varied to alter the intensity of support to the arch of the foot.

In alternative embodiments, the dynamic foot-arch support device 100 is utilized with other anchor components such as, but not limited to, a shoe, sock, or stocking. For example, in one embodiment, the forefoot portion 118, 128 of the support band is placed to rest under the $2^{nd}$ through the $4^{th}$ or $5^{th}$ metatarsal phalange distal heads and securely attached to an inner sole surface of a shoe. The tension is formed on the support band between the inside sole area and the loop around an area about or just below an ankle portion of the foot providing support to the plantar surface.

Alternatively, the dynamic foot-arch support device 100, as a whole, is integrally formed with a sock or stocking. A wearer of such a support device 100 simply pulls on the device as a sock or stocking and the arch support structure is already integrated.

Figure 3:
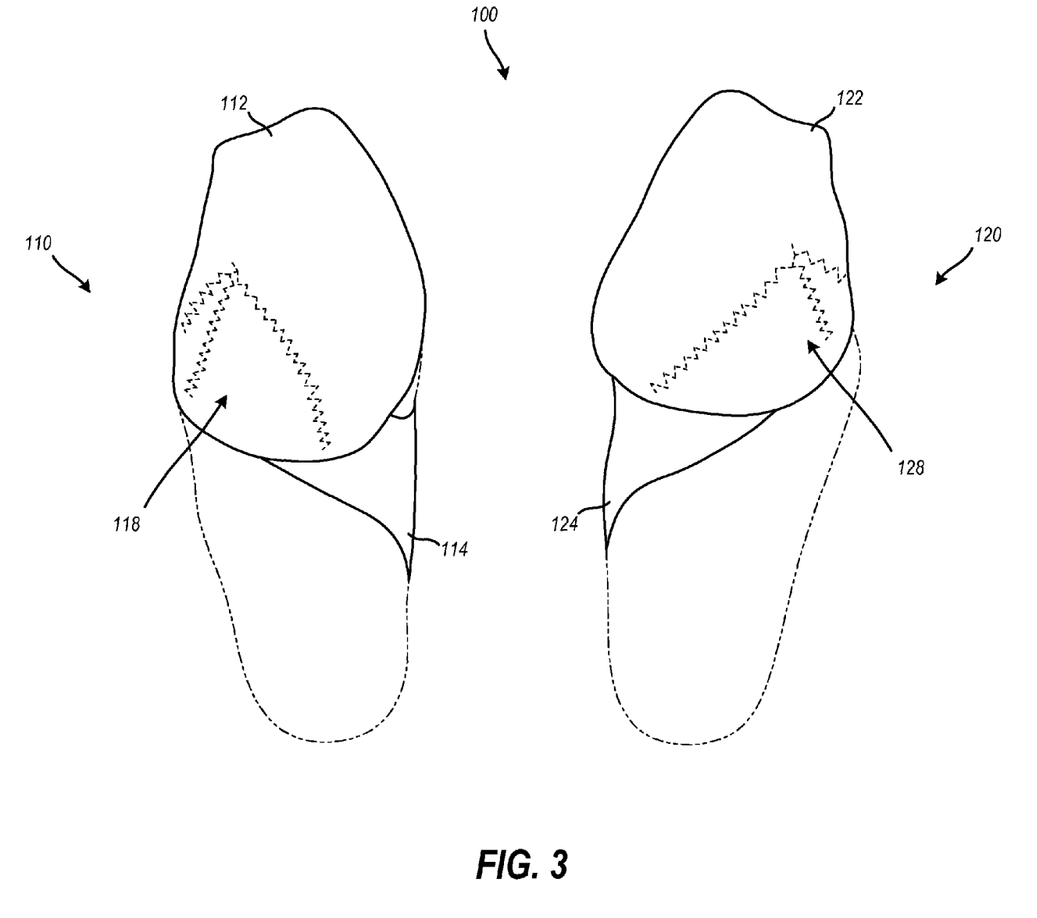
FIG. 3 is a bottom view of the dynamic foot-arch support device depicted in FIG. 1.

With reference now to FIG. 3, the dynamic foot-arch support device 100 is shown, in a bottom view, with the support band 102, 104 and attached forefoot cover 112, 122 in place on a left foot 120 and right foot 110. The forefoot portion 118, 128 of the support band is securely attached to the forefoot cover 112, 122 by means of a particular stitching pattern. Alternative methods for attachment can be utilized so long at the attachment is secure and not obtrusive to the foot. The forefoot portion 118, 128 of the support band is securely attached to the forefoot cover 112, 122 at a predetermined angle to maximize support to the arch portion of the foot.

Figure 4:
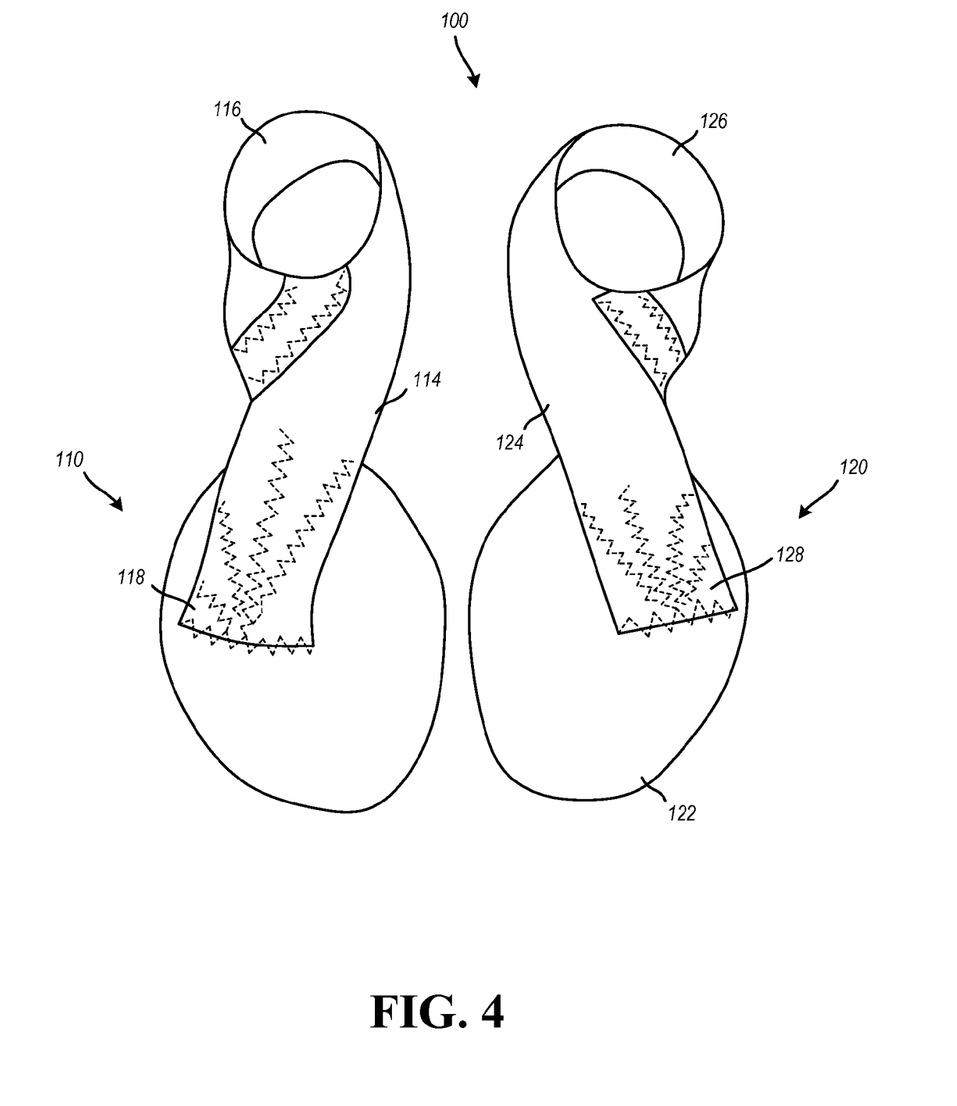
FIG. 4 is an inside, front view of the dynamic foot-arch support device depicted in FIG. 1.

With reference now to FIG. 4, the dynamic foot-arch support device 100 is shown, in a front, inside view, with the support band 102, 104 and attached forefoot cover 112, 122 in place on a left foot 120 and right foot 110.

Figure 5:
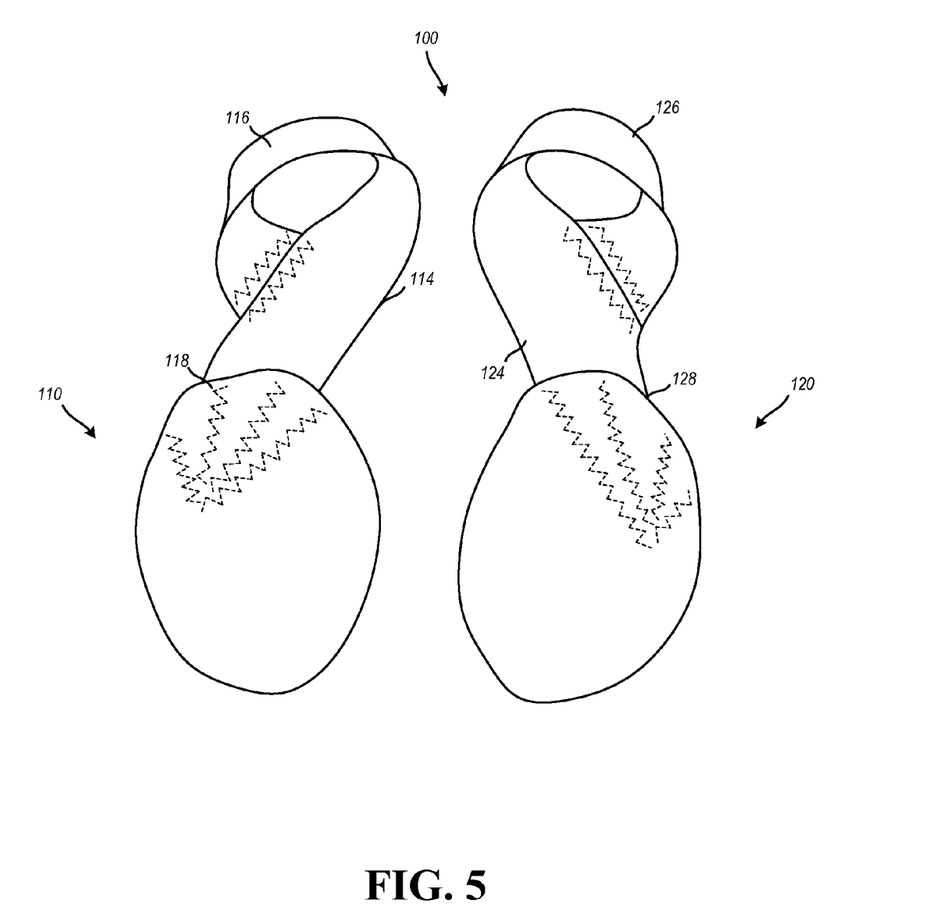
FIG. 5 is a back, inside view of the dynamic foot-arch support device depicted in FIG. 1.

With reference now to FIG. 5, the dynamic foot-arch support device 100 is shown, in a back, inside view, with the support band 102, 104 and attached forefoot cover 112, 122 in place on a left foot 120 and right foot 110. The forefoot portion 118, 128 of the support band is securely attached to the forefoot cover 112, 122 by means of a particular stitching pattern. The support band 102, 104 is shown looped and attached to a lateral side by stitching. Alternative methods for attachment can be utilized so long at the attachment of the support band 102, 104 is secure and not obtrusive to the foot.

Figure 6:
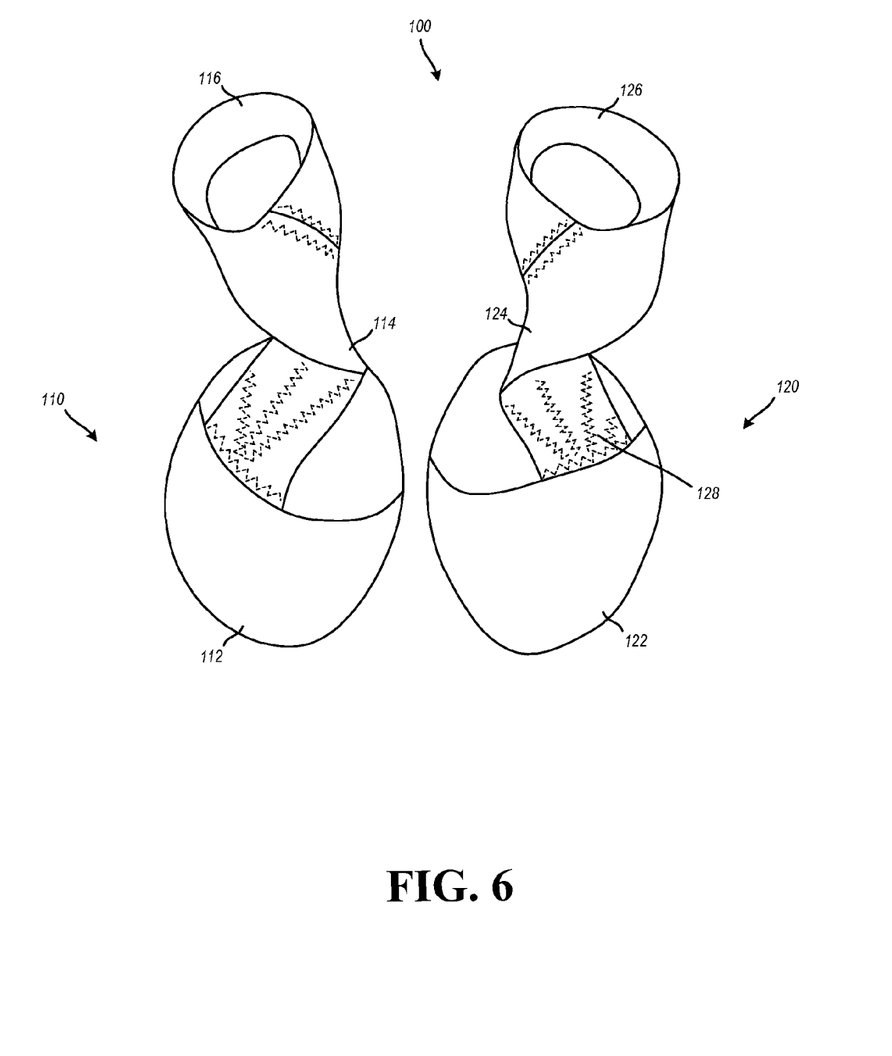
FIG. 6 is a top, front view of the dynamic foot-arch support device depicted in FIG. 1, illustrating, in particular, a rotation to provide the wearer with foot and arch support, according to an embodiment of the technology.

With reference now to FIG. 6, the dynamic foot-arch support device 100 is shown, in a top, front view, illustrating a rotation of the support band 102, 104. By way of example, a wearer of the dynamic foot-arch support device 100 with a forefoot cover 112, 122 places the support band 102, 104 on each foot 110, 120 and then rotates the support band 102, 104 for 180 degrees of rotation and placing the support band 102, 104 on the medial arch before placing the forefoot cover 112, 122 over the toes on each foot. As shown, the medial arch portion 114, 124 receives much of the force of the rotation and thereby adds tension and support to the arch of the foot.

Figure 7:
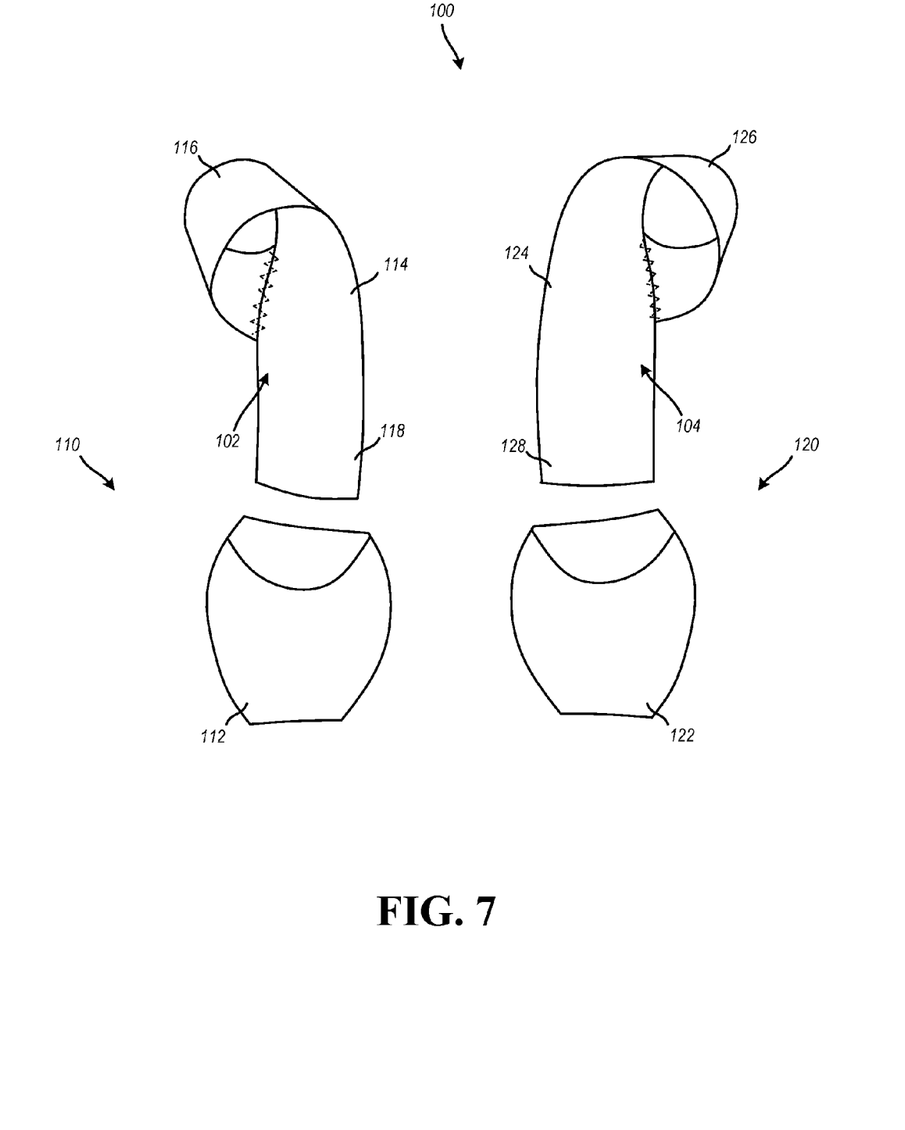
FIG. 7 is a top view of the dynamic foot-arch support device depicted in FIG. 1 illustrating, in particular, the band and forefoot cover according to an embodiment of the technology.

With reference now to FIG. 7, support band 102, 104 is shown unattached from any anchor device. The support band can be attached to the forefoot cover 112, 122 or to another anchor device such as a shoe, or the like. Additionally, the support band 102, 104 can be integrally formed with a sock, stocking, or the like.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. A dynamic foot-arch support device for dynamically supporting the arch and structures of a foot throughout phases of the biomechanical movement of the foot during weight-bearing activities, the device comprising:

a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide a tension to support to an arch area of the foot; and a forefoot cover securely attached to the lower end of the support band at a predetermined angle and configured for placement over a toe area of the foot, wherein the toe area comprises an area over all toes of the foot, and wherein the support band is integrally formed with a sock.

2. A dynamic foot-arch support device for dynamically supporting the arch and structures of a foot throughout phases of the biomechanical movement of the foot during weight-bearing activities, the device comprising:

a support band having a generally rectangular shape having a length and a width, comprised of an elongated, flexible material that is elastic in length and inelastic in width, an upper end and a lower end, the support band forming a fixed loop at the upper end through which to place a foot and position the fixed loop around an area about or just below an ankle portion of the foot, the lower end configured to wrap from an inside of the area about or just below the ankle portion of the foot and rotate 180 degrees to an underside of the foot and across a plantar surface area for secure attachment below the underside of the foot, the support band thereby configured to provide a tension to support to an arch area of the foot; and a forefoot cover securely attached to the lower end of the support band at a predetermined angle and configured for placement over a toe area of the foot, wherein the toe area comprises an area over all toes of the foot, and wherein a length of the support band is adjustable to accommodate varying foot sizes.

* * * * *